United States Patent [19]

Commons et al.

[11] Patent Number: 5,373,009
[45] Date of Patent: Dec. 13, 1994

[54] DIBENZOFURANYL ESTERS OF N-HETEROCYCLIC CARBOXYLIC ACIDS

[75] Inventors: Thomas J. Commons, Wayne; Donald P. Strike, St. Davids, both of Pa.

[73] Assignee: American Home Products Corporation, Madison, N.J.

[21] Appl. No.: 190,416

[22] Filed: Feb. 2, 1994

[51] Int. Cl.$^5$ .................. A61K 31/54; A61K 31/535; C07D 295/205; C07D 211/06
[52] U.S. Cl. ........................ 514/228.2; 514/232.8; 514/278; 514/320; 544/6; 544/58.4; 544/172; 546/16; 546/196; 548/147; 548/201; 548/215; 548/216; 548/407; 548/525
[58] Field of Search ............... 544/6, 58.4, 71, 172; 546/16, 196; 548/407, 525, 147, 201, 215, 216; 514/228.2, 320, 278, 232.8

[56] References Cited

U.S. PATENT DOCUMENTS

| | | | |
|---|---|---|---|
| 3,819,683 | 6/1974 | Krebs et al. | 260/279 C |
| 3,819,683 | 6/1974 | Krebs et al. | 260/479 |
| 3,846,445 | 11/1974 | Bondesson et al. | 260/315 |
| 3,897,453 | 7/1975 | Gante et al. | 260/329.3 |
| 5,066,674 | 11/1991 | Quinn | 514/529 |
| 5,169,844 | 12/1992 | Commons et al. | 514/211 |

FOREIGN PATENT DOCUMENTS 0116234 8/1984 European Pat. Off. .

Primary Examiner—Mukund J. Shah
Assistant Examiner—Matthew V. Grumbling
Attorney, Agent, or Firm—Richard K. Jackson

[57] ABSTRACT

A compound of the formula:

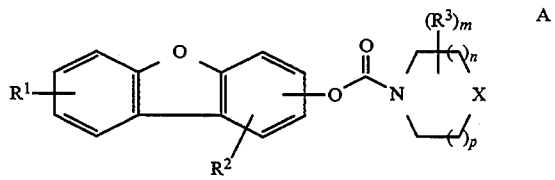

wherein
$R_1$ and $R_2$ are, independently, halo, trifluoromethyl, cyano, nitro, alkyl, alkoxy, —$CO_2H$, alkylcarbonyl, alkylcarbonyloxy, alkoxycarbonyl, mono- or di-alkylaminocarbonyl, or mono- or di-alkylaminocarbonyloxy;
m is 0, 1 or 2 and
$R^3$ is alkyl;
n and p are, independently, 0, 1 or 2;
X is O, S or $CR^4R^5$,
where $R^4$ and $R^5$ are, independently, H or alkyl or $R^4$ and $R^5$ together with the interposed carbon atom form a 3 to 8 membered carbocyclic ring, are anti-cholesterolemic agents.

7 Claims, No Drawings

DIBENZOFURANYL ESTERS OF N-HETEROCYCLIC CARBOXYLIC ACIDS

BACKGROUND OF THE INVENTION

U.S. Pat. No. 3,819,683 discloses dibenzylfuryl N-methyl carbamate as an intermediate to be used in the preparation of an N-acylated final product of unknown utility. The compounds involved in the present application are not capable of acylation.

U.S. Pat. No. 5,169,844 discloses 4-[[methylamino)-carbonyl]oxy]-1-piperidinecarboxylic acid 4-phenoxyphenyl ester as a CEH inhibitor.

DESCRIPTION OF THE INVENTION

In accordance with this invention there is provided a series of novel compounds which inhibit cholesterol absorption and have the general formula A.

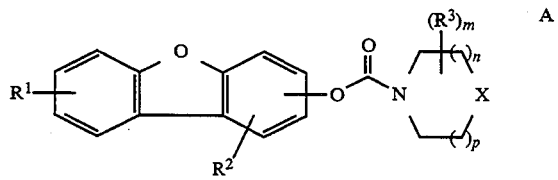

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl, in which each alkyl group has 1 to 6 carbon atoms, or mono- or di-alkylaminocarbonyloxy in which each alkyl group has 1 to 6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring.

The compounds of this invention inhibit the absorption of cholesterol from the intestinal tract. As indicated in Table I below, the compounds are inhibitors of cholesterol ester hydrolase (CEH). It has been shown that removal of this enzyme from pancreatic juice results in an 80% reduction in the uptake of cholesterol into the bloodstream in rats [Hosie et al, J. Biol. Chem., 262, 260 (1987)]. The association between high serum cholesterol levels and coronary heart disease is well documented. Consequently, compounds that prevent the uptake of cholesterol are useful for treating atherosclerosis, familial hypercholesterolemia, hyperlipemia, and like diseases.

Hence, this invention also provides a method for reducing cholesterol uptake from the intestinal tract which comprises administering, orally or parenterally, to an animal in need of reduced cholesterol absorption, a compound of formula A:

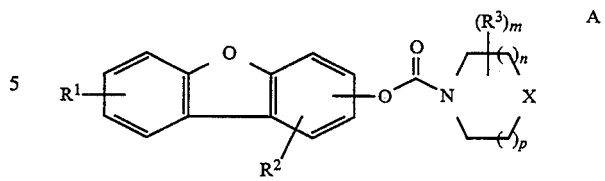

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl,
in which each alkyl group has 1 to 6 carbon atoms, or mono- or di-alkylaminocarbonyloxy in which each alkyl group has 1 to 6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring.

In addition this invention provides pharmaceutical compositions comprising a compound of formula A:

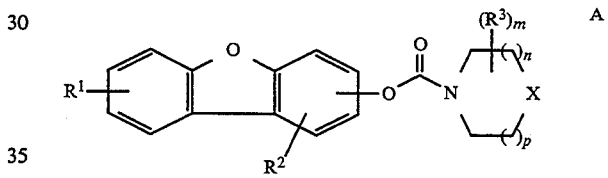

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl, in which each alkyl group has 1 to 6 carbon atoms, or mono- or di-alkylaminocarbonyloxy in which each alkyl group has 1 to 6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring;
and a pharmaceutically acceptable carder.

The compounds of this invention are conveniently prepared by either one of two methods. In the first method a carbamoyl chloride is reacted with the appropriate hydroxydibenzofuran in the presence of a base in a suitable solvent (Scheme I). In the second method the appropriate hydroxydibenzofuran is first convened in situ to its chloroformate using phosgene or a phosgene equivalent. Reaction of the chloroformate with the desired amine in the presence of a base in a suitable solvent gives the desired product. A suitable phosgene equivalent is trichloromethyl chloroformate. This route is outlined in Scheme II. Specific examples of the routes illustrated in Schemes I and II are given in the Experimental Section.

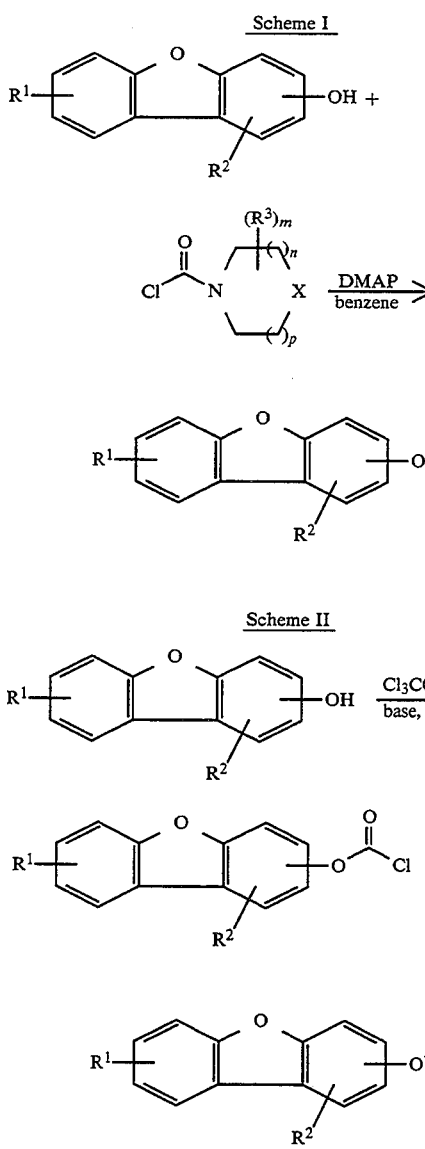

Scheme I

Scheme II

The specific examples for the synthesis of the invention compounds given in the Experimental Section are for illustrative purposes only and are not to be construed as limiting this disclosure in any way. Those skilled in the art will be aware of other methods of preparing compounds of this invention. The starting materials or intermediates are available commercially or can be prepared by standard literature procedures.

The in vitro and in vivo standard test procedures are given below and the biological results are presented in Table I.

In Vitro Standard Test Procedure

The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.1.1.13) Sigma Company, St. Louis, Mo., U.S.A., No. C-1892, from bovine pancreas] and measuring the amount of ester formed, according to the procedure of Field, J. of Lipid Research, 25, 389 (1984). The concentration of test compound that inhibits one-half of the ester formation ($IC_{50}$) is given in Table I.

In Vivo Standard Test Procedure

The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20, 162 (1979). The serum radioactivity was measured at six hours after dosing. The results of this study are reported in Table I as percent decrease compared to control.

TABLE I

| EXAMPLE | In Vitro Results $IC_{50}$ ($\mu$m) CEH | In Vivo Results Effect on Absorption of $^{14}$C-chol-6 hr-normal rat % Decrease (mg/kg) |
|---|---|---|
| 1 | 1.4 | 49% (10) |
| 2 | 0.51 | 16% (10) |
| 3 | 6.5 | 44% (3) |
| 4 | 15 | 55% (3) |

Experimental Section

EXAMPLE 1

4-Methyl-1-piperidinecarboxylic acid 2-dibenzofuranyl ester

A mixture of 2-hydroxydibenzofuran (10.0 g, 54.3 mmol), dimethylaminopyridine (DMAP) (7.3 g, 59.8 mmol) and 4-methyl-1-piperidinecarbonyl chloride (8.8 ml, 59.7 mmol) in 200 mL of benzene was refluxed under nitrogen for 7 hours. The reaction was extracted with 1N HCl and then the organic layer was dried (MgSO$_4$) and the solvent removed under reduced pressure to give 17.51 g of a light brown solid. Recrystallization of the solid from diisopropyl ether gave 10.82 g (64%) of the title compound as a light brown crystalline solid, mp 123°–125° C.

Elemental analysis for $C_{19}H_{19}NO_3$ Calc'd: C, 73.77; H, 6.19; N, 4.53 Found: C, 73.77; H, 6.27; N, 4.60

EXAMPLE 2

4-Thiomornholinecarboxylic acid 2-dibenzofuranyl ester

A solution of 2-hydroxydibenzofuran (5.0 g, 27 mmol) and dimethylaniline (3.4 mL, 27 mmol) in 35 mL of tetrahydrofuran(THF) plus 1.5 mL of dioxane was added dropwise under nitrogen to a solution of trichloromethyl chloroformate (1.6 mL, 14 mmol) in 30 mL of tetrahydrofuran at ice bath temperature. After the addition the cooling bath was removed and the stirring continued for approximately 24 hours. The reaction was cooled to ice bath temperature and a solution of thiomorpholine (2.7 mL, 27 mmol) and pyridine (4.4 mL, 54 mmol) in 30 mL of tetrahydrofuran was added dropwise over 15 minutes. After the addition the reaction was stirred at ice bath temperature for 2 hours. The cooling bath was removed and the stirring continued for approximately 22 hours. The reaction was diluted with ethyl acetate, extracted two times with 1N HCl, dried (MgSO$_4$) and the solvent removed under reduced pressure to give 6.99 g of a yellow solid. Purification of this solid by chromatography on silica gel using hexane-methylene chloride as the eluent and then recrystallization of the material isolated from diisopropyl ether gave 1.90 g (22%) of the title compound as a white crystalline solid, mp 142°–143° C.

Elemental analysis for $C_{17}H_{15}NO_3S$ Calc'd: C, 65.16; H, 4.82; N, 4.47 Found: C, 64.87; H, 5.10; N, 4.38

EXAMPLE 3

4,4-Dimethyl-1-piperidinecarboxylic acid 2-dibenzofuranyl ester

In the same manner as described in Example 2, and replacing the thiomorpholine with 4,4-dimethylpiperidine, the title compound was produced as a white crystalline solid (1.35 g, 39%) after purification of the crude reaction by chromatography on silica gel (230–400 mesh) using hexane—ethyl acetate as the eluent and then recrystallization of the material isolated from diisopropyl ether, mp 128°–129° C.

Elemental analysis for $C_{20}H_{21}NO_3$ Calc'd: C, 74.28; H, 6.55; N, 4.33 Found: C, 74.19; H, 6.50; N, 4.26

EXAMPLE 4

8-Azaspiro[4,5]decane-8-carboxylic acid 2-dibenzofuranyl ester

In the same manner as described in Example 2, and replacing the thiomorpholine with 8-azaspiro[4.5]decane, the title compound was produced as a white crystalline solid (1.17 g 45%) after purification of the crude reaction by chromatography on silica gel (230–400 mesh) using hexane—ethyl acetate as the eluent and then recrystallization of the material isolated from diisopropyl ether, mp 153°–154° C.

Elemental analysis for $C_{22}H_{23}NO_3$ Calc'd: C, 75.62; H, 6.63; N, 4.01 Found: C, 75.58; H, 6.59; N, 4.06

What is claimed is:

1. A compound of the formula:

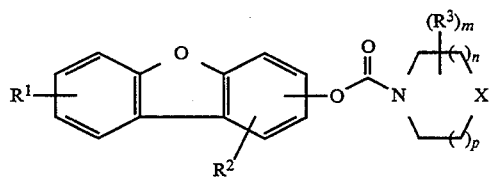

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl, in which each alkyl group has 1 to 6 carbon atoms, or mono- or di-alkylaminocarbonyloxy in which each alkyl group has 1 to 6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring.

2. The compound of claim 1 which is 4-methyl-1-piperidinecarboxylic acid 2-dibenzofuranyl ester.

3. The compound of claim 1 which is 4-thiomorpholinecarboxylic acid 2-dibenzofuranyl ester.

4. The compound of claim 1 which is 4,4-dimethyl-1-piperidinecarboxylic acid 2-dibenzofuranyl ester.

5. The compound of claim 1 which is 8-azaspiro[4.5]decane-8-carboxylic acid 2-dibenzofuranyl ester.

6. A method for reducing cholesterol uptake from the intestinal tract which comprises administering, orally or parenterally, to an animal in need of reduced cholesterol absorption, a compound of formula A:

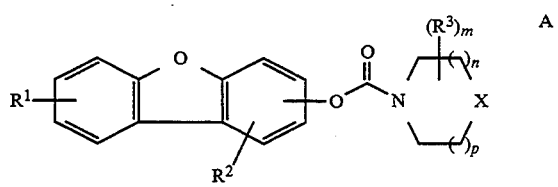

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl, in which each alkyl group has 1–6 carbon atoms, or mono- or di-alkylaminocarbonyloxy in which each alkyl group has 1–6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring.

7. A pharmaceutical composition comprising a compound of formula A:

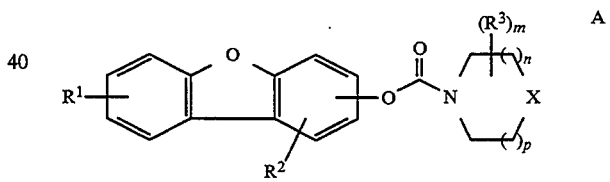

wherein
- $R_1$ and $R_2$ are, independently, fluorine, chlorine, bromine, iodine, trifluoromethyl, cyano, nitro, $C_1$–$C_6$ alkyl, $C_1$–$C_6$ alkoxy, —$CO_2H$, $C_2$–$C_7$ alkylcarbonyl, $C_2$–$C_7$ alkylcarbonyloxy, $C_2$–$C_7$ alkoxycarbonyl, mono- or di-alkylaminocarbonyl, in which each alkyl group has 1–6 carbon atoms, or mono- or di-alkylaminocarbonyloxy in which each alkyl group has 1–6 carbon atoms;
- m is 0, 1 or 2 and $R^3$ is $C_1$–$C_6$ alkyl;
- n and p are, independently, 0, 1 or 2;
- X is O, S or $CR^4R^5$, where $R^4$ and $R^5$ are, independently, H or $C_1$–$C_6$ alkyl or $R^4$ and $R^5$ together with the interposed carbon atom form a 3 to 8 membered carbocyclic ring;

and a pharmaceutically acceptable carder.

* * * * *